(12) United States Patent
Platzek et al.

(10) Patent No.: US 7,326,798 B2
(45) Date of Patent: Feb. 5, 2008

(54) CHIRAL HEPTYNE DERIVATIVES FOR THE PREPARATION OF EPOTHILONES AND PROCESSES FOR THEIR PREPARATION

(75) Inventors: Johannes Platzek, Berlin (DE); Orlin Petrov, Berlin (DE); Marc Willuhn, Berlin (DE); Klaus Dieter Graske, Berlin (DE); Werner Skuballa, Berlin (DE)

(73) Assignee: Schering AG, Berlin (DE)

( * ) Notice: Subject to any disclaimer, the term of this patent is extended or adjusted under 35 U.S.C. 154(b) by 407 days.

(21) Appl. No.: 11/110,959

(22) Filed: Apr. 21, 2005

(65) Prior Publication Data

US 2006/0100442 A1    May 11, 2006

Related U.S. Application Data

(60) Provisional application No. 60/565,849, filed on Apr. 28, 2004.

(30) Foreign Application Priority Data

Apr. 22, 2004    (EP) .................................. 04090157

(51) Int. Cl.
*C07D 309/06*    (2006.01)
*C07C 45/27*    (2006.01)
(52) U.S. Cl. ....................................... 549/423; 568/391
(58) Field of Classification Search ................ 549/423; 568/391

See application file for complete search history.

(56) References Cited

U.S. PATENT DOCUMENTS 6,320,045 B1    11/2001    Johnson et al.

FOREIGN PATENT DOCUMENTS

WO    WO 99/59985    11/1999
WO    WO 01/73103    10/2001

*Primary Examiner*—Taofiq Solola
(74) *Attorney, Agent, or Firm*—Millen, White, Zelano, Branigan, P.C.

(57) ABSTRACT

The invention relates to a new synthetic process for the production of key intermediates useful in the synthesis of epothilones or epothilone derivatives, to certain compounds used to produce these key intermediates and to a process to produce said compounds.

24 Claims, No Drawings

CHIRAL HEPTYNE DERIVATIVES FOR THE PREPARATION OF EPOTHILONES AND PROCESSES FOR THEIR PREPARATION

This application claims the benefit of the filing date of U.S. Provisional Application Ser. No. 60/565,849 filed Apr. 28, 2004 which is incorporated by reference herein.

The invention relates to a new synthetic process for the production of key intermediates useful in the synthesis of epothilones or epothilone derivatives, to certain compounds used to produce these key intermediates and to a process to produce said compounds. The process for the production of the key intermediates starts from readily available and cheap starting materials, yields products in high enantiomeric purity, in high chemical purity, in good yields and allows an industrial-scale production.

The invention is used in the synthesis of structural unit B of natural and synthetically-modified epothilones or derivatives. Epothilones are 16-membered macrolide compounds that find utility in the pharmaceutical field. Epothilones have been isolated from cultures of *Myxobacterium Sorangium Cellosum* and are representatives of a class of promising anti-tumor agents that were tested and found to be effective against a number of cancer lines. A survey of the syntheses for these compounds has been described by J. Mulzer et al. in *Monatsh. Chem.* 2000, 131, 205-238. These agents have the same biological mode of action as paclitaxel and other taxanes (see for paclitaxel, D. G. I. Kingston, *Chem. Commun.* 2001, 867-880), however, epothilones have also been shown to be active against a number of resistant cell lines (see S. J. Stachel et al., *Curr. Pharmaceut. Design* 2001, 7, 1277-1290; K.-H. Altmann, *Curr. Opin. Chem. Biol.* 2001, 5, 424-431).

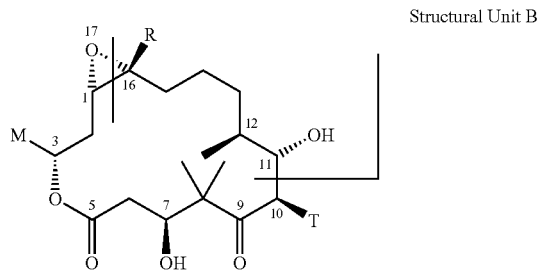

Structural Unit B

In addition to natural epothilones, the literature describes a number of synthetic epothilone derivatives that vary for the most part in radicals M, T and R. In most cases, M stands for a heterocyclic radical. For natural epothilone A, R stands for hydrogen, whereas for epothilone B, R stands for methyl.

Most syntheses of the natural epothilones and the synthetic epothilone derivatives involve the joining of several structural units. Structural unit B, which represents the $C_{11}$-$C_{16}$ fragment, proved to be one of the strategically important structural units. It was, therefore, of great importance to develop an economical process for the production of structural unit B of epothilone syntheses.

In most cases, the epothilone is synthesized by inserting structural unit B as a protected hydroxy ketone (formula I, $X_1$=protecting group). The $C_1$-$C_{16}$ linkage is carried-out by means of a Wittig reaction, while the $C_{10}$-$C_{11}$ linkage is carried-out by means of an aldol reaction. Both reactions have already been described in the literature (see K. C. Nicolaou et al., *Tetrahedron* 1998, 54, 7127-7166; *Angew. Chem.* 1998, 110, 85-89; *Chem. Eur. J.* 1997, 3, 1971-1986; *J. Am. Chem. Soc.* 1997, 119, 7974-7991).

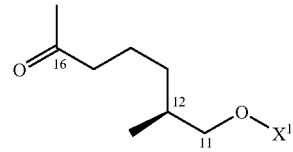

A possible preparation of structural unit B is described in, for example, WO 99/07692 and WO 00/47584. However, the syntheses presented there are expensive and based on the introduction of chirality using an expensive chiral auxiliary agent and thus not usable or feasible for an industrial-scale production of epothilone or epothilone derivatives.

WO 98/25929 and K. C. Nicolaou et al., *J. Am. Chem. Soc.* 1997, 119, 7974-7991 also describe tedious preparations of structural unit B by means of a chiral auxiliary agent. These preparations have additionally the technical disadvantage of introducing chirality at a reaction temperature of −100° C.

A further synthesis is described in *Helv. Chim. Acta* 1990, 73, 733-738, whereby a compound of formula I ($X_1$=H) is also used. This compound, however, is obtained from a costly synthesis involving diterpenes as starting materials (see also *Chimia* 1973, 27, 97-99) and results in an enantiomeric purity of only approx. 80 to 85%.

Moreover, it can be said that the processes described in the literature require a purification process involving several chromatographic steps, which is rather disadvantageous from a production stand point because this results in many general technical problems such as reconditioning of solvents, avoiding contamination of the environment, high cost, etc.

Due to low total yields, low space-time yields and high excesses of reagents, it has not been possible with any of the processes available to a person skilled in the art to economically prepare structural unit B on an industrial-scale. There was therefore a need for such an industrial-scale process and capable of being implemented on an operational scale, that allows for a universally usable intermediate compound for the production of structural unit B in the total synthesis of epothilones and epothilone derivatives.

The goal of the present invention is to provide a novel synthetic process for the production of intermediates used in the synthesis of epothilones and epothilone derivatives. In contrast to other published syntheses, the new route starts from economical starting materials, yields intermediate products in high enantiomeric purity, in high chemical purity, in good yields and allows an industrial-scale production. The prior art has the disadvantage of requiring either the use of expensive chiral auxiliary agents (in some cases at a temperature of −100° C.), expensive starting materials, or expensive purification process. Therefore, the new synthesis offers many important advantages.

The present invention relates to a synthetic route for the production of compounds of general formula IA, a key structural unit used in total epothilone or epothilone derivatives syntheses:

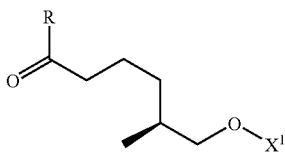

IA wherein

R is selected from the group consisting of hydrogen, alkyl, and substituted alkyl, alkyl being preferred; and $X^1$ is an oxygen protecting group.

The compounds of formula IA can then be used for the synthesis of epothilones and epothilone derivatives via various steps known in the art.

The invention also relates to new compounds of general formulas II and III used for the production of compounds of general formula IA and to a process described herein for the production of these new compounds:

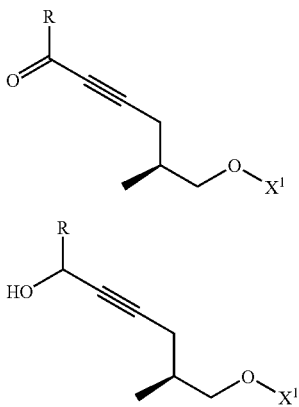

II

III wherein R and $X^1$ have the same meaning as hereinbefore given under formula IA.

The invention especially relates to the synthesis of the compounds of formula IA (see reaction sequence) starting from compounds of general formula IV, a synthesis which is largely unrelated to any synthesis found in the literature related to epothilone syntheses and which has many important advantages:

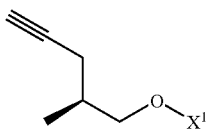

IV wherein $X^1$ has the same meaning as hereinbefore given under formula IA.

Within the present description, the general definitions used hereinbefore and hereinafter preferably have the following meaning:

Alkyl can be a linear or branched alkyl, preferably having up to and including 12 carbon atoms. Examples of alkyl groups are linear alkyls such as methyl, ethyl, n-propyl, n-butyl, n-pentyl, n-hexyl, n-heptyl, n-octyl, n-nonyl, n-decyl, n-undecyl or n-dodecyl group or branched alkyl groups such as the iso-propyl, iso-butyl, sec-butyl, tert-butyl, iso-pentyl, neo-pentyl, 2-pethylpentyl, 2,2-dimethylbutyl, 2,3-dimethylbutyl, 2-methylhexyl, 2,2-dimethylpentyl, 2,2,3-trimethylbutyl or 2,3,3-trimethylbutyl group. Especially preferred are methyl and ethyl.

Examples of a substituted alkyl include —$CH_2$-Halogen or —C(Halogen)$_3$, especially preferred are —$CH_2F$ and $CF_3$.

A protecting group can be selected from the group comprising a silyl protecting group such as trimethylsilyl, tert-butyidimethylsilyl, triethylsilyl, tri(iso-propyl)silyl, dimethylphenylsilyl; lower alkanoyl, such as acetyl; benzoyl; tetrahydropyranyl; Mom protecting group, Mem protecting group; benzyl or substituted benzyl radicals such as 4-methoxybenzyl; or any other protecting group known from the literature (see for example T. W. Green, *Protective Groups in Organic Synthesis*, John Wiley & Sons N.Y., 1981; P. J. Kocienski, *Protecting Groups*, Georg Thieme Verlag Stuttgart, 1994). Preferred are tetrahydropyranyl (THP) and tert-butyldimethylsilyl (TBDMS), with THP being especially preferred.

The process steps making up the process of the invention and the preferred aspects thereof can be described preferably as follows:

The reaction sequence starts with a compound of general formula IV as hereinbefore described which is reacted with an aldehyde of general formula V:

RCHO    V wherein R is as hereinbefore described, under reaction conditions known to a person skilled in the art for such acetylene additions to aldehydes (see Shun, Annabelle L. K. Shi et al., *J. Org. Chem.*, 2003, 68, 4, 1339-1347; Mukai, Chisato et al., *J. Org. Chem.*, 2003, 68, 4, 1376-1385; Clark, J. Stephen et al. *Org. Lett.*, 2003, 5, 1, 89-92; Chun, Jiong et al., *J. Org. Chem.*, 2003, 68, 2, 348-354; Nomura, Izumi et al., *Org. Lett.*, 2002, 4, 24, 4301-4304; Nielsen, Thomas E. et al., J. Org. Chem., 2002, 67, 18, 6366-6371; Kiyota, Hiromasa et al., *Syn. Lett.*, 2003, 2, 219-220; Bailey et al., *J. Chem. Soc.*, 1957, 3027, 3031; Nayler et al., *J. Chem. Soc.*, 1955, 3037, 3045; Moureu, *Bull. Soc. Chim. Fr.*, 33, 155; Theus et al., *Helv. Chim. Acta*, 1955, 38, 239, 249; Gredy, C. R. *Hebd. Seances Acad. Sci.*, 1934, 199, 153; Ann. Chim. (Paris), <11> 4, 1935, 5, 36); preferably the alkyne is deprotonated at a temperature between −78 to 0° C. in an aprotic solvent, such as methyl-tert-butyl ether, 2-methyl-THF, dioxane, toluene, or THF, with a strong base such as BuLi, LDA or Li, Na, K-HMDS, or Grignard solution, such as MeMgCl, MeMgBr or isopropyl-MgBr, and subsequently added to the aldehyde, yielding a compound of general formula III as hereinbefore described; compound of general formula III is then oxidized with an oxidizing agent known to a person skilled in the art (see for example Shun, Annabelle L. K. Shi et al., *J. Org. Chem.*, 2003, 68, 4, 1339-1347; Clark, J. Stephen et al., *Org. Lett.*, 2003, 5, 1, 89-92; Chun, Jiong et al., *J. Org. Chem.*, 2003, 68, 2, 348-354; Quesnelle, Claude A. et al., *Bioorg. Med. Chem. Lett.*, 2003, 13, 3, 519-524; Barriga, Susana et al., *J. Org. Chem.*, 2002, 67, 18, 6439-6448; Suzuki, Keisuke et al., *Org. Lett.*, 2002, 4, 16, 2739-2742; Claeys, Sandra et al., *Eur. J. Org. Chem.*, 2002, 6, 1051-1062; Tanaka, Katsunao et al., *Bioorg. Med. Chem. Lett.*, 2002, 12, 4, 623-628; Rodriguez, David et al., *Tetrahedron Lett.*, 2002, 43, 15, 2717-2720; Tanaka, Koichi et al., *J. Chem. Soc. Perkin*

*Trans.*, 2002, 1, 6, 713-714; Hao, Junliang et al., *Tetrahedron Lett.*, 2002, 43, 1, 1-2; Hiegel et al., Synthetic Commun., 1992, 22(11), 1589; De Mico et al., *J. Org. Chem.*, 1997, 62, 6974), especially manganese dioxide in THF, TEMPO oxidation, trichloroisocyanuric acid or under Swern oxidation conditions, to yield a compound of general formula II as hereinbefore described; the triple bond of compound of general formula II is then reduced using processes known to a person skilled in the art (see for example Crombie et al., *J. Chem. Soc.*, 1958, 4435, 4443; Braude et al., *J. Chem. Soc.*, 1949, 607, 613; Taber, Douglass F. et al., *J. Org. Chem.*, 2002, 67, 23, 8273-8275; Bowden et al., *J. Chem. Soc.*, 1946, 52; Fazio, Fabio et al., *Tetrahedron Lett.*, 2002, 43, 5, 811-814; Gonzalez, Isabel C. et al. *J. Amer. Chem. Soc.*, 2000, 122, 38, 9099-9108; Brimble, Margaret A. et al. *Aust. J. Chem.*, 2000, 53, 10, 845-852); preferably the reduction is done under catalytic hydrogenation conditions, using Pd on carbon in THF, as well as in the presence of acetic acid esters, lower alcohols such as methanol, ethanol, isopropanol, 2-methyl-THF, at a temperature between 0 to 50° C., under 5 to 10 bar of pressure, and for a period of 1 to 10 hours, to yield a compound of general formula IA.

Compounds of general formula IV are known in the literature and can be prepared according to methods known to a person skilled in the art such as:

For $X^1$=TBS: Ireland, Robert E. et al., *Tetrahedron*, 1997, 53, 39, 13221-13256; Bhatt, Ulhas et al., *J. Org. Chem.*, 2001, 66, 5, 1885-1893; Yan, Jingbo et al., *J. Org. Chem.*, 1999, 64, 4, 1291-1301.

For $X^1$=benzyl: Takle, Andrew et al., *Tetrahedron*, 1990, 46, 13/14, 4503-4516; Ireland, Robert E. et al., *J. Org. Chem.*, 1992, 57, 19, 5071-5073.

For $X^1$=tert-butyldiphenylsilyl: Culshaw, David et al., *Tetrahedron Lett.*, 1985, 26, 47, 5837-5840.

For $X^1$=MOM: Williams, David R. et al., *J. Amer. Chem. Soc.*, 1989, 111, 5, 1923-1925.

For $X^1$=THP: Baker, Raymond et al., *Tetrahedron Lett.*, 1986, 27, 28, 3311-3314; Ireland, Robert E. et al., *Tetrahedron*, 1997, 53, 39, 13221-13256.

Alternatively, compounds of general formula II can be directly obtained by the reaction of a compound of general formula IV as hereinbefore described with an activated acid derivative of general formula VI,

VI wherein R is as hereinbefore described, and X is an appropriate leaving group, preferably halogen, —OCOR$_1$, OR$_1$, imidazole, 4-nitrophenol, Weinreb residue, —N(R$_1$)$_2$ or mixed anhydrides, wherein R$_1$ is alkyl. Compounds of general formula II are then subsequently converted to compounds of general formula IA as hereinbefore described in the reaction sequence. The reaction of compounds such as IV and VI has, for example, been described in the following literature:

Naka, Tadaatsu et al., *Tetrahedron Lett.*, 2003, 44, 3, 443-446;

Nielsen, Thomas E. et al., *J. Org. Chem.*, 2002, 67, 21, 7309-7313;

Hakogi, Toshikazu et al., *Bioorg. Med. Chem. Lett.*, 2003, 13, 4, 661-664;

Nielsen, Thomas E. et al., *J. Org. Chem.*, 2002, 67, 21, 7309-7313; and

Knoelker, Hans-Joachim et al., *Tetrahedron*, 2002, 58, 44, 8937-8946.

It also proved to be advantageous in some cases to prepare compounds of general formula IA directly from compounds of general formula VII,

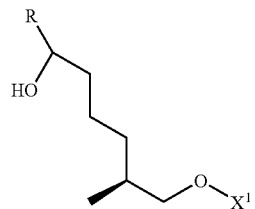

VII by oxidating compounds of general formula VII using methods for the oxidation of secondary alcohols known to a person skilled in the art (see literature cited above).

Compounds of general formula VII are obtained from compounds of general formula III by reduction of the triple bond according to the methods hereinbefore described.

Another alternative, is the hydrogenation of compounds of general formula II to corresponding alkenes of general formula VIII,

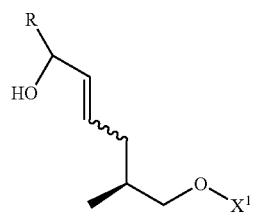

VIII followed by the oxidation of the corresponding alkenes, and their subsequent further hydrogenation to compounds of the general formula IA, or if the allyl alcohol VII directly rearranges, compounds of general formula IA can be obtained as is described, for example in Paul, C. R. *Hebd. Seances Acad. Sci.*, 1939, 208, 1320; *Bull. Soc. Chim. Fr.*, 1941, <5>8, 509; and Cheeseman et al., *J. Chem. Soc.*, 1949, 2034; Uma, Ramalinga et al., *Eur. J. Org. Chem.*, 2001, 10, 3141-3146; Cherkaoui, Hassan et al., *Tetrahedron*, 2001, 57, 12, 2379-2384; Lee, Donghyun et al., *Org. Lett.*, 2000, 2, 15, 2377-2380.

The reactions described above are preferably carried out under the conditions analogous to those given in the examples. The following examples are intended to illustrate the invention without being intended to restrict the scope of the invention:

EXAMPLES

Example 1 a) (2RS,6S)-6-Methyl-7-[(RS)-(3,4,5,6-tetrahydro-2H-pyran-2-yl)oxy]hept-3-in-2-ol 2450 ml n-BuLi solution, 1.6 M, in hexane is added dropwise to a 650 g solution (3.566 mol) of (RS)-2-{[(S)-

2-methylpent-4-in-1-yl]oxy}-3,4,5,6-tetrahydro-2H-pyrane (prepared in accordance with Ireland, Robert E. et al., *Tetrahedron*, 1997, 53, 39, 13221-13256.) in 325 ml of THF at −10° C. A solution of 310 g acetaldehyde in 1200 ml THF is then added dropwise. After 30 min., 3250 ml MTBE (methyl-tert.butylether) is added and 3250 ml 10% aq NH₄Cl is added and further stirred for 10 min. The organic phase is washed twice with 1300 ml H₂O each and concentrated in vacuo to dryness. 930 g of product is obtained. The obtained product is directly used in the subsequent step.

Yield: approx. 100% (according to DC quantitatively) Elementary Analysis

| Calc. | C 68.99 | H 9.80 |
| --- | --- | --- |
| Found | C 68.75 | H 10.03 |

¹H-NMR (CD₂Cl₂), 400 MHz 1H (ppm)/number of H 1.00 (3H) 1.4 (3H) 1.50-1.83 (6H) 1.92 (1H) 2.15+2.33 (2H) 3.25+3.6 (2H) 3.45+3.85 (2H) 4.48 (1H) 4.56 (1H)

b) (S)-6-Methyl-7-[(RS)-(3,4,5,6-tetrahydro-2H-pyran-2-yl)oxy]hept-3-in-2-one

A 300 g (1.3255 mol) solution of (2RS,6S)-6-methyl-7-[(RS)-(3,4,5,6-tetrahydro-2H-pyran-2-yl)oxy]hept-3-in-2-ol, dissolved in 600 ml of THF, is added by stirring to a suspension of 1500 g manganese dioxide in 2250 ml of THF, and stirring is continued at room temperature for 48 hours. The suspension is then filtered over silica gel and the solvent is removed in vacuo. 280 g of the product is obtained.

Yield: 94.1% of the theory Elementary analysis:

| Calc. | C 69.61 | H 8.99 |
| --- | --- | --- |
| Found | C 69.42 | H 9.16 |

¹H-NMR (CD₂Cl₂), 400 MHz 1H (ppm)/number of H 1.03 (3H) 1.5-1.85 (6H) 2.04 (1H) 2.3 (3H) 2.35+2.53 (2H) 3.2-3.3+3.6-3.65 (2H) 3.5+3.8 (2H) 4.55 (1H)

c) (S)-6-Methyl-7-[(RS)-(3,4,5,6-tetrahydro-2H-pyran-2-yl)oxy]heptan-2-one

A 50 g solution (222.9 mmol) of (S)-6-methyl-7-[(RS)-(3,4,5,6-tetrahydro-2H-pyran-2-yl)oxy]hept-3-in-2-one and 5 g palladium on carbon (10% Pd/C) in 400 ml of THF is hydrogenated for one hour at 8 bar hydrogen at room temperature. The catalyst is then filtered off, rewashed with little solvent and the solvent is removed in vacuo. 50.9 g of product is obtained.

Yield: approx. 100% of the theory. (According to DC quantitatively) Elementary analysis:

| Calc. | C 68.38 | H 10.59 |
| --- | --- | --- |
| Found | C 68.18 | H 10.71 |

¹H-NMR (CDCl₃), 400 MHz 1H (ppm)/number of H 0.91/0.93 (3H) 1.0-1.9 (11H) 2.13 (3H) 2.42 (2H) 3.19 (1H) 3.4-3.6 (2H) 3.85 (1H) 4.55 (1H)

Example 2

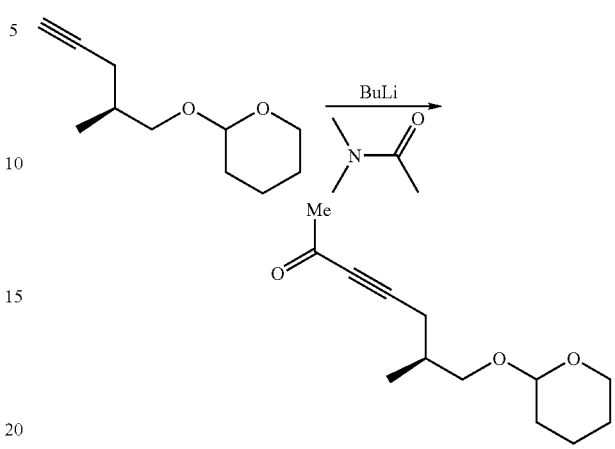

(S)-6-Methyl-7-[(RS)-(3,4,5,6-tetrahydro-2H-pyran-2-yl)oxy]hept-3-in-2-on

To a solution of 100.0 g (RS)-2-{[(S)-2-Methylpent-4-in-1-yl]oxy}3,4,5,6-tetrahydro-2H-pyran (Ireland, Robert E. et al., *Tetrahedron*, 1997, 53, 39, 13221-13256) in 200 ml THF were added, dropwise at −30° C., 439 ml n-butyllithium (15% in hexane). The solution was stirred for 20 minutes at −30° C. and 20 minutes at −20° C. After cooling to −30° C., a solution of 95.6 g N,N-dimethylacetamide in 200 ml THF was added during 15 minutes and the reaction mixture was stirred for 30 minutes at −20°. The reaction mixture was then poured into a stirred precooled (0° C.) mixture of 1000 ml hexane and a solution of 104,8 g citric acid monohydrate in 700 ml water. The aqueous phase was separated and the organic phase was washed with 300 ml water and then filtered over 100 g silica gel. The silica gel was washed with 1000 ml hexane. The combined eluates were reduced to an oil by vacuum distillation.

Yield: 116,9 g (95%). C₁₃H₂₀O₃ MW: 224.30 g/mol Elemental analysis

| Calc. | C 69.61 | H 8.99 |
| --- | --- | --- |
| Found | C 69.44 | H 9.19 |

¹H-NMR (CD₂Cl₂), 400 MHz 1H (ppm)/number of H 1.03 (3H) 1.5-1.85 (6H) 2.04 (1H) 2.3 (3H) 2.35+2.53 (2H) 3.2-3.3+3.6-3.65 (2H) 3.5+3.8 (2H) 4.55 (1H)

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding European application No. 04090157.1, filed Apr. 22, 2004, and U.S.

Provisional Application Ser. No. 60/565,849, filed Apr. 28, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing a compound represented by formula IA,

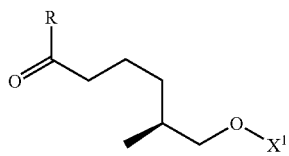

IA wherein R is selected from the group consisting of hydrogen, alkyl, and substituted alkyl; and $X^1$ is an oxygen protecting group;

comprising reacting a compound of formula IV,

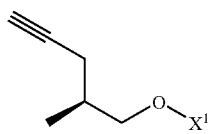

IV wherein $X^1$ is as defined above, with an aldehyde of formula V,

RCHO      V wherein R is as defined above, in the presence of a suitable base to form a compound of formula III,

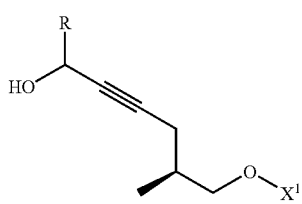

III wherein R and $X^1$ are as defined above, reacting compound of formula III with a suitable oxidizing agent to form a compound of formula II,

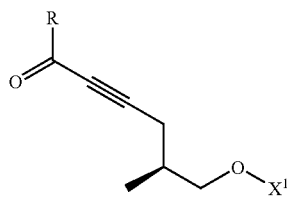

II wherein R and $X^1$ are as defined above, and subsequently reacting compound II with a suitable reducing agent to form said compound of formula IA.

2. A process for preparing a compound represented by formula IA,

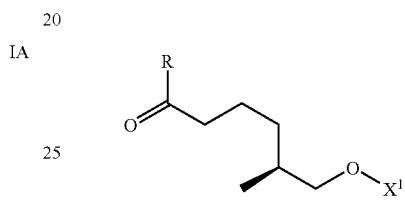

IA wherein R is selected from the group consisting of hydrogen, alkyl, and substituted alkyl; and $X^1$ is an oxygen protecting group;

comprising reacting a compound of formula IV,

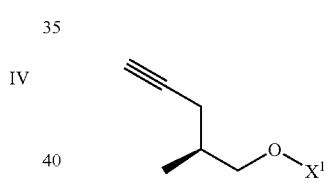

IV wherein $X^1$ is as defined above, with an activated acid derivative of formula VI,

VI wherein R is as described above; and X is an leaving group, in the presence of a suitable base to form a compound of formula II,

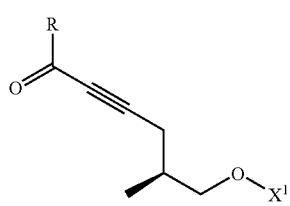

II wherein R and X¹ are as defined above, and subsequently reacting the compound of formula II with a suitable reducing agent to form said compound of formula IA.

3. A process for preparing a compound represented by formula IA,

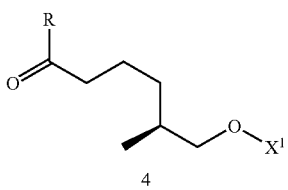

IA wherein R is selected from the group consisting of hydrogen, alkyl, and substituted alkyl; and X¹ is an oxygen protecting group;
comprising reacting a compound of formula III,

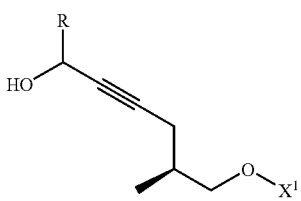

III wherein R and X¹ are as described above, with a suitable reducing agent to form a compound of formula VII,

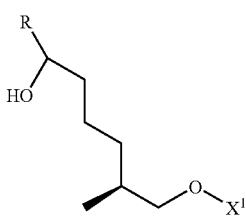

VII wherein R and X¹ are as described above, and then subsequently reacting the said compound of formula VII with a suitable oxidizing agent to form said compound of formula IA.

4. A process for preparing a compound represented by formula IA,

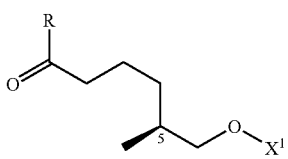

IA wherein R is selected from the group consisting of hydrogen, alkyl, and substituted alkyl; and X¹ is an oxygen protecting group;

comprising reacting a compound of formula II,

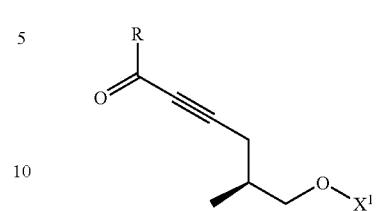

II wherein R and X¹ are as described above, with a suitable reducing agent to form a compound of formula VIII,

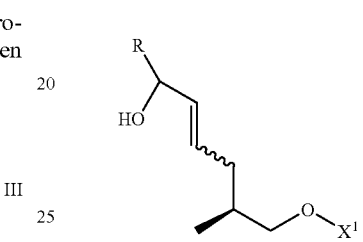

VIII wherein R and X¹ are as described above, then subsequently reacting the said compound of formula VIII with a suitable oxidizing agent and then a suitable reducing agent to form said compound of formula IA; or alternatively, the compound of formula VIII directly rearranges to the compound of formula IA.

5. A process according to claim 2, wherein X is halogen, —$OCOR_1$, $OR_1$, imidazole, 4-nitrophenol, a Weinreb residue, —$N(R_1)_2$, or mixed anhydrides and wherein $R_1$ is alkyl.

6. A process according to claim 2, wherein X is Cl or Br.

7. A process according to claim 2, wherein X is —OCOMe or OMe.

8. A process according to claim 2, wherein X is —$N(CH_3)_2$.

9. A process according to claim 1, wherein R is alkyl.

10. A Process according to claim 1, wherein R is $CH_3$.

11. A process according to claim 1, wherein X¹ is THP or TBDMS.

12. A process according to claim 1, wherein X¹ is THP.

13. A compound of formula II,

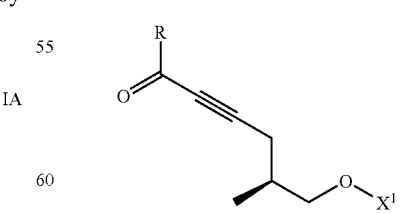

II wherein:
R is selected from the group consisting of hydrogen, alkyl, and substituted alkyl; and, $X_1$ is an oxygen protecting group.

14. A compound of formula III,

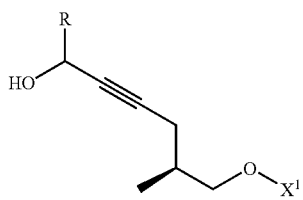

wherein:
R is selected from the group consisting of hydrogen, alkyl, and substituted alkyl; and, $X_1$ is an oxygen protecting group.

15. A compound according to claim 13, wherein R is alkyl.
16. A compound according to claim 13, wherein R is $CH_3$.
17. A compound according to claim 13 wherein $X^1$ is THP or TBDMS.
18. A compound according to claim 13, wherein $X^1$ is THP.
19. A compound according to claim 14, wherein R is alkyl.
20. A compound according to claim 19, wherein R is $CH_3$.
21. A compound according to claim 14, wherein $X^1$ is THP or TBDMS.
22. A compound according to claim 14, wherein $X^1$ is THP.

23.

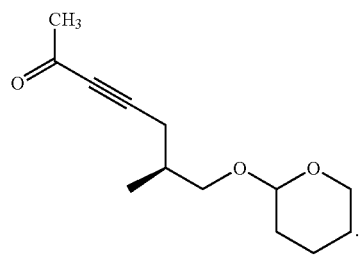

24.

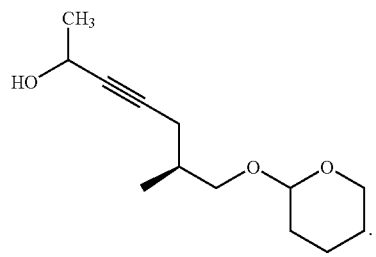

* * * * *